US011103232B2

(12) United States Patent
Kim (10) Patent No.: US 11,103,232 B2
(45) Date of Patent: *Aug. 31, 2021

(54) KNOTLESS SUTURE, AND KIT CONTAINING SAME

(71) Applicant: Y.JACOBS MEDICAL INC., Seoul (KR)

(72) Inventor: Young Jae Kim, Seoul (KR)

(73) Assignee: Y.JACOBS MEDICAL INC., Seoul (KR)

(*) Notice: Subject to any disclaimer, the term of this patent is extended or adjusted under 35 U.S.C. 154(b) by 375 days.

This patent is subject to a terminal disclaimer.

(21) Appl. No.: 15/897,086

(22) Filed: Feb. 14, 2018

(65) Prior Publication Data

US 2018/0168567 A1    Jun. 21, 2018

Related U.S. Application Data

(63) Continuation of application No. 15/340,784, filed on Nov. 1, 2016, now Pat. No. 9,924,937, which is a
(Continued)

(30) Foreign Application Priority Data

Dec. 27, 2011   (KR) .................. 10-2011-0143929

(51) Int. Cl.
*A61B 17/04* (2006.01)
*A61B 17/06* (2006.01)

(52) U.S. Cl.
CPC .......... *A61B 17/0401* (2013.01); *A61B 17/04* (2013.01); *A61B 17/0487* (2013.01);
(Continued)

(58) Field of Classification Search
CPC ............ A61B 17/0401; A61B 17/0487; A61B 17/06166; A61B 2017/0403;
(Continued)

(56) References Cited

U.S. PATENT DOCUMENTS 3,123,077 A   3/1964 Alcamo
3,981,307 A   9/1976 Borysko
(Continued)

FOREIGN PATENT DOCUMENTS

CN       101219066 A    7/2008
CN     2012166619 Y    4/2009
(Continued)

OTHER PUBLICATIONS

Office Action of Japanese Patent Application No. 2018-197450—3 pages (dated Nov. 6, 2018).
(Continued)

*Primary Examiner* — Majid Jamialahmadi
(74) *Attorney, Agent, or Firm* — K&L Gates LLP (57) ABSTRACT

The present invention relates to a suture which is firmly maintained and fixed to an operation site to stably sustain suturing or lifting effects for a long time. More specifically, the present invention provides a suture having a conic or pyramidal shape with a cut top, wherein a suture supporter comprising a communication hole penetrating the both ends is provided at one end. The suture support can have one or more portions which are cut vertically from a lower end at a lower end portion having a larger diameter between the both ends, or a part of the lower end can be removed so as to form one or more gaps formed from the end at a wall of the end portion.

13 Claims, 5 Drawing Sheets

Related U.S. Application Data continuation of application No. 14/368,997, filed as application No. PCT/KR2012/011361 on Dec. 24, 2012, now Pat. No. 9,480,473.

(52) U.S. Cl.
CPC ...... *A61B 17/06166* (2013.01); *A61B 2017/0409* (2013.01); *A61B 2017/0438* (2013.01); *A61B 2017/0462* (2013.01); *A61B 2017/0464* (2013.01); *A61B 2017/06057* (2013.01); *A61B 2017/06176* (2013.01)

(58) Field of Classification Search
CPC .... A61B 2017/0404; A61B 2017/0406; A61B 2017/0408; A61B 2017/0409; A61B 2017/0411; A61B 2017/0412; A61B 2017/0414; A61B 2017/0427; A61B 2017/06052; A61B 2017/0417; A61B 2017/06176
See application file for complete search history.

(56) References Cited

U.S. PATENT DOCUMENTS

| | | | |
|---|---|---|---|
| 4,744,364 A | 5/1988 | Kensey | |
| 4,805,292 A | 2/1989 | Noguchi | |
| 4,822,904 A | 4/1989 | Davidson | |
| 4,932,962 A | 6/1990 | Yoon et al. | |
| 5,041,129 A | 8/1991 | Hayhurst et al. | |
| 5,053,046 A | 10/1991 | Janese | |
| 5,053,047 A | 10/1991 | Yoon | |
| 5,080,667 A | 4/1992 | Chen et al. | |
| 5,192,301 A | 3/1993 | Kamiya et al. | |
| 5,207,694 A | 5/1993 | Broome | |
| 5,224,955 A | 7/1993 | West | |
| 5,236,443 A | 8/1993 | Sontag | |
| 5,259,846 A | 11/1993 | Granger et al. | |
| 5,269,809 A | 12/1993 | Hayhurst | |
| 5,306,294 A | 4/1994 | Winston et al. | |
| 5,330,503 A | 7/1994 | Yoon | |
| 5,500,000 A | 3/1996 | Feagin | |
| 5,626,614 A | 5/1997 | Hart | |
| 5,643,295 A | 7/1997 | Yoon | |
| 5,683,417 A | 11/1997 | Cooper | |
| 5,741,299 A | 4/1998 | Rudt | |
| 5,931,855 A | 8/1999 | Buncke et al. | |
| 6,241,747 B1 | 6/2001 | Ruff | |
| 6,939,326 B1 | 9/2005 | Thappa | |
| 7,056,331 B2 | 6/2006 | Kaplan et al. | |
| 7,468,068 B2 | 12/2008 | Kolster | |
| 7,582,105 B2 | 9/2009 | Kolster | |
| 7,601,164 B2 | 10/2009 | Wu | |
| 7,967,841 B2 | 6/2011 | Yuan | |
| 7,988,727 B2 | 8/2011 | Santamore | |
| 8,192,462 B2 | 6/2012 | Sulamanidze et al. | |
| 8,747,438 B2 | 6/2014 | Longo et al. | |
| 8,758,367 B2 | 6/2014 | Philippon et al. | |
| 9,044,224 B2 | 6/2015 | Lauria | |
| 9,125,647 B2 | 9/2015 | Goraltchouk et al. | |
| 9,204,965 B2 | 12/2015 | Longoria | |
| 9,480,473 B2 * | 11/2016 | Kim .................. A61B 17/04 | |
| 9,575,341 B2 | 2/2017 | Heck et al. | |
| 9,808,234 B2 * | 11/2017 | Kim .................. A61B 17/062 | |
| 9,848,865 B2 | 12/2017 | Kim | |
| 9,924,937 B2 | 3/2018 | Kim | |
| 10,010,317 B2 | 7/2018 | Kim | |
| 10,178,990 B2 | 1/2019 | Kim | |
| 10,226,320 B2 | 3/2019 | Kim | |
| 2002/0198544 A1 | 12/2002 | Uflacker | |
| 2003/0149447 A1 * | 8/2003 | Morency .......... A61B 17/06166 606/228 | |
| 2004/0030319 A1 | 2/2004 | Korkor et al. | |
| 2004/0030354 A1 | 2/2004 | Leung et al. | |
| 2004/0153102 A1 | 8/2004 | Therin et al. | |
| 2005/0101984 A1 | 5/2005 | Chanduszko et al. | |
| 2005/0240224 A1 | 10/2005 | Wu | |
| 2005/0245963 A1 | 11/2005 | Kida et al. | |
| 2006/0079935 A1 | 4/2006 | Kolster | |
| 2006/0135994 A1 | 6/2006 | Ruff et al. | |
| 2006/0135996 A1 | 6/2006 | Schwartz et al. | |
| 2006/0265010 A1 | 11/2006 | Paraschac et al. | |
| 2007/0038249 A1 * | 2/2007 | Kolster ............ A61B 17/06166 606/228 | |
| 2007/0049971 A1 | 3/2007 | Chin et al. | |
| 2007/0167958 A1 | 7/2007 | Sulamanidze et al. | |
| 2007/0213770 A1 | 9/2007 | Dreyfuss | |
| 2008/0058816 A1 | 3/2008 | Philippon et al. | |
| 2008/0132943 A1 | 6/2008 | Maiorino et al. | |
| 2008/0228144 A1 | 9/2008 | Liniger et al. | |
| 2008/0281357 A1 | 11/2008 | Sung et al. | |
| 2009/0088797 A1 | 4/2009 | Crombie et al. | |
| 2009/0093670 A1 | 4/2009 | Annest et al. | |
| 2009/0112259 A1 | 4/2009 | D'Agostino | |
| 2009/0210003 A1 | 8/2009 | Sulamanidze et al. | |
| 2009/0299407 A1 | 12/2009 | Yuan et al. | |
| 2010/0137679 A1 | 6/2010 | Lashinski et al. | |
| 2010/0160961 A1 | 6/2010 | Nawrocki et al. | |
| 2011/0054522 A1 | 3/2011 | Lindh et al. | |
| 2011/0238111 A1 | 9/2011 | Frank | |
| 2011/0270304 A1 | 11/2011 | Lee | |
| 2011/0276090 A1 | 11/2011 | Berndt et al. | |
| 2011/0282386 A1 | 11/2011 | Friedrich et al. | |
| 2011/0288563 A1 | 11/2011 | Gianotti et al. | |
| 2012/0109193 A1 | 5/2012 | Primavera et al. | |
| 2012/0109195 A1 | 5/2012 | Odermatt et al. | |
| 2012/0239002 A1 | 9/2012 | Griswold | |
| 2013/0245684 A1 | 9/2013 | Ruff et al. | |
| 2013/0345745 A1 | 12/2013 | Kim | |
| 2014/0155913 A1 | 6/2014 | Kim | |
| 2014/0228971 A1 | 8/2014 | Kim | |
| 2014/0364904 A1 | 12/2014 | Kim | |
| 2015/0305736 A1 | 10/2015 | Kim | |
| 2015/0366553 A1 | 12/2015 | Kim | |
| 2016/0242899 A1 | 8/2016 | Lee et al. | |
| 2016/0302905 A1 | 10/2016 | Kim | |
| 2018/0116648 A1 | 5/2018 | Kim | |
| 2018/0303477 A1 | 10/2018 | Kim | |

FOREIGN PATENT DOCUMENTS

| | | |
|---|---|---|
| CN | 101500495 A | 8/2009 |
| CN | 201692490 U | 1/2011 |
| CN | 102271734 A | 12/2011 |
| DE | 3223153 C1 | 8/1983 |
| DE | 102008057213 A1 | 5/2010 |
| EP | 314412 A1 | 5/1989 |
| EP | 1929961 A2 | 6/2008 |
| EP | 1955720 A1 | 8/2008 |
| EP | 2020209 A1 | 2/2009 |
| EP | 2108316 A1 | 10/2009 |
| EP | 2386252 A1 | 11/2011 |
| EP | 2386323 A2 | 11/2011 |
| GB | 1091282 A | 11/1967 |
| JP | 2-45703 U | 3/1990 |
| JP | 04-250151 A | 9/1992 |
| JP | 04-307050 A | 10/1992 |
| JP | 04-307052 A | 10/1992 |
| JP | 08-52154 A | 2/1996 |
| JP | 08-140982 A | 6/1996 |
| JP | 02-277459 B2 | 5/1998 |
| JP | 10-258123 A | 9/1998 |
| JP | 10-272182 A | 10/1998 |
| JP | 2000-202029 A | 7/2000 |
| JP | 3069906 U | 7/2000 |
| JP | 2000-225118 A | 8/2000 |
| JP | 2000-232984 A | 8/2000 |
| JP | 2002-516585 A | 6/2002 |
| JP | 2003-019683 A | 1/2003 |
| JP | 2004-041492 A | 2/2004 |
| JP | 2004-057516 A | 2/2004 |
| JP | 2004-073403 A | 3/2004 |
| JP | 2004-121634 A | 4/2004 |
| JP | 2004-530524 A | 10/2004 |

(56) References Cited

FOREIGN PATENT DOCUMENTS

| | | |
|---|---|---|
| JP | 2004-329964 A | 11/2004 |
| JP | 2005-177499 A | 7/2005 |
| JP | 2005-177500 A | 7/2005 |
| JP | 2006-025867 A | 2/2006 |
| JP | 2006-515203 A | 5/2006 |
| JP | 2006-516902 | 7/2006 |
| JP | 2007-075616 A | 3/2007 |
| JP | 2007-090062 A | 4/2007 |
| JP | 2007-522837 A | 8/2007 |
| JP | 2007-537017 A | 12/2007 |
| JP | 2008-114074 A | 5/2008 |
| JP | 2008-514382 A | 5/2008 |
| JP | 2008-132327 A | 6/2008 |
| JP | 2008-132328 A | 6/2008 |
| JP | 2008-132329 A | 6/2008 |
| JP | 2008-546454 A | 12/2008 |
| JP | 2009-517156 A | 4/2009 |
| JP | 2009-531071 A | 9/2009 |
| JP | 2009-247890 A | 10/2009 |
| JP | 2009-279393 A | 12/2009 |
| JP | 2010-500102 A | 1/2010 |
| JP | 2010-507453 A | 3/2010 |
| JP | 2010-518902 A | 6/2010 |
| JP | 2010-537676 A | 12/2010 |
| JP | 2011-500208 A | 1/2011 |
| JP | 2011-240133 A | 12/2011 |
| JP | 2011-240134 A | 12/2011 |
| JP | 2012-515015 A | 7/2012 |
| JP | 2014-514017 | 6/2014 |
| JP | 6410980 B2 | 10/2018 |
| KR | 10-178358 B1 | 4/1998 |
| KR | 20-0287634 Y1 | 8/2002 |
| KR | 20-0320005 Y1 | 7/2003 |
| KR | 10-0473108 B1 | 3/2005 |
| KR | 10-2005-0108494 A | 11/2005 |
| KR | 10-0761921 B1 | 10/2007 |
| KR | 10-2008-0039345 A | 5/2008 |
| KR | 10-2009-0035692 A | 4/2009 |
| KR | 10-2009-0103639 A | 10/2009 |
| KR | 10-2010-0120642 A | 11/2010 |
| KR | 20-0451570 Y1 | 12/2010 |
| KR | 10-2011-0019895 A | 3/2011 |
| KR | 10-1044731 B1 | 6/2011 |
| KR | 10-1057376 B1 | 8/2011 |
| KR | 10-1105647 B1 | 1/2012 |
| KR | 10-2012-0010049 A | 2/2012 |
| KR | 10-1132841 B1 | 4/2012 |
| KR | 10-1155817 B1 | 6/2012 |
| KR | 10-1182337 B1 | 9/2012 |
| KR | 10-1185583 B1 | 9/2012 |
| KR | 10-1326736 B1 | 11/2013 |
| KR | 10-1326763 B1 | 11/2013 |
| KR | 10-1367902 B1 | 2/2014 |
| KR | 10-1455206 B1 | 10/2014 |
| SU | 700121 A1 | 11/1979 |
| SU | 1178420 A1 | 2/1984 |
| SU | 1360705 A1 | 7/1986 |
| WO | 2006/109377 A1 | 10/2006 |
| WO | 2007/098212 A2 | 8/2007 |
| WO | 2008/020937 A2 | 2/2008 |
| WO | 2008/057261 A2 | 5/2008 |
| WO | 2008/103308 A1 | 8/2008 |
| WO | 2009/027883 A2 | 3/2009 |
| WO | 2009/055105 A1 | 4/2009 |
| WO | 2010/028324 A2 | 3/2010 |
| WO | 2010/052006 A1 | 5/2010 |
| WO | 2010/062743 A2 | 6/2010 |
| WO | 2010/080014 A2 | 7/2010 |
| WO | 2011/128392 A1 | 10/2011 |
| WO | 2011/139916 A2 | 11/2011 |
| WO | 2012/121538 A2 | 9/2012 |
| WO | 2012/144677 A1 | 10/2012 |
| WO | 2013/169075 A1 | 11/2013 |
| WO | 2015/083864 A1 | 6/2015 |

OTHER PUBLICATIONS

Office Action of corresponding Japanese Patent Application No. 2020-003171—4 pages (dated Apr. 7, 2020).
Office Action dated Jan. 12, 2016 of corresponding Japanese Patent Application No. 2015-241510—2 pages.
Application of related U.S. Appl. No. 15/102,240.
Karam et al., "Curved Stylet Core Biopsy Results in Larger Cores", American Journal of Roentgenology, Jul. 2010, vol. 195, pp. 242-244.
"MediFirst Homepage", http://www.medifirst.co.kr, printed on or before Nov. 5, 2013.
BD Product Catalog, Jan. 2010, BD Medical.
Optinova ICM (TM) IV-catheter tubing, 2007, Optimus Nova.
John Jacobs Medical, "Youngs Lift", Jun. 7, 2012.
Catheter, http://ko.wikipedia.org/wiki/%EC%B9%B4%ED%85%8C%ED%84%B0?oldid=13222103, printed Aug. 24, 2015.
I.V. Catheter, Production Introduction, htt://www.dukwooco.co.kr/english/product/pro_1.htm, Dukwoo Medical Co., Ltd., printed on Apr. 9, 2016.
Prado et al., "Supplemental Fixation After Endoscopic Brow Elevation Using a Single Nylon Suture", printed from QMP's Plastic Surgery Pulse News, 2010, vol. 2, No. 1, Quality Medical Publishing, St. Louis, obtained from.
Polydioxanone Sutre, Metro Korea, downloaded from http://www.metrokr.com/shop/goods/goods_view.php?goodsno=186785506&category=004 on or before Oct. 30, 2015.
Safelock Catheter, LKMEDICAL Co., Ltd. Product Catalog, downloaded from http://www.lkmedical.com on or before Oct. 30, 2015.
Qosina, Thousands of Stock Components, 2014, Qosina Product Catalog.
Angiocatheter, http://medical-dictionary.thefreedictionary.com/angiocatheter, The Free Dictionary, downloaded on or before Oct. 2, 2015.
Food and drug safety-wife medical equipment e-petitions, Ministry of Food and Drug Safety, downloaded from http://www.emed.mfds.go.kr/ on or before Nov. 3, 2015.
Office Communication Japanese Patent Office on third party submission of references in Japanese Patent Application 2014-549981 dated Jan. 25, 2016—20 pages.
Product Photos, Jul. 18, 2006, BD Inc., downloaded on or before Oct. 8, 2014.
Office Action dated May 30, 217 of corresponding Japanese Patent Application No. 2016-148772—6 pages.
Office Action of Japanese Patent Application No. 2016-250538 corresponding to copending U.S. Appl. No. 16/020,769—4 pages (dated Aug. 23, 2018)
Office Action of corresponding Japanese Patent Application No. 2018-178273—4 pages (dated May 14, 2019).
Office Action of Japanese Patent Application No. 2018-091563 corresponding to the related application, U.S. Appl. No. 15/853,634—6 pages (dated Jul. 24, 2018).
Notice of Reasons for Refusal of Japanese Patent Application No. 2017-132746—4 pages (dated Nov. 6, 2020).

* cited by examiner

KIT A (b)

KIT B

KNOTLESS SUTURE, AND KIT CONTAINING SAME

INCORPORATION BY REFERENCE

Any and all applications for which a foreign or domestic priority claim is identified in the Application Data Sheet as filed with the present application are hereby incorporated by reference under 37 CFR 1.57.

FIELD

The present invention relates to a suture used for a surgical operation, and more particularly, to a suture that does not require a knot tying operation and is able to be firmly and stably sutured or to tightly support and fix tissues.

BACKGROUND

A suture has been used for a long time to be used to connect and suture damaged muscles, blood vessels, nerves, or tissues and injuries or parts incised due to a surgical operation. In addition, a suture is used for a double eyelid surgery and a medical operation for removing tissues, which are generated due to aging, a decrease in skin elasticity, injuries, overdose, necrosis, or the like, a flabby skin, wrinkles, or the like. A lifting medical operation using a suture is a technology to lift up a flabby skin or tissue such as a face, a chin, a neck, an abdomen, a vagina, a breast, or a hip by using needles and threads instead of using a knife. The lifting medical operation using a suture has attracted much attention because the lifting medical operation does not excessively incise a skin, minimizes generation of scars, and generates less bleeding and swelling due to an operation.

Recently, a suture in which barbs are formed on an external surface thereof has been developed and used. Such a suture is not slipped due to the barbs, and thus the suture is not easily untied after a sutura.

One of points to be considered in an operation using a suture that is firmly maintained and fixed at a part where a surgical operation has been performed, in order to stably maintain suturing and tight adhesion, supporting, and fixing of tissues. In addition, a firm knotting device for allowing a suture not to be untied is required, and also it is necessary to minimize time and efforts on knotting for a rapid and safe operation.

The inventors of the present invention applied for Korean Patent Application Nos. 10-2011-0019895 and 10-2011-0064084 for a suture including a suture supporter not requiring a knotting process, and the contents thereof are introduced in the present specification. The inventors of the present invention have conducted the study in order to invent a more convenient and useful suture.

DETAILED DESCRIPTION

Technical Problem

The present invention provides a suture that may be more firmly maintained and fixed at a part where a surgical operation has been performed, may stably maintain suturing and tight adhesion, supporting, and fixing of tissues by effectively holding the tissues. The present invention also provides a suture not requiring a knotting process. The present invention also provides a kit including a suture.

Technical Solution

According to an aspect of the present invention, there is provided a suture including first and second ends, and a suture supporter that is disposed at the first end of the suture and has a truncated conical shape or a truncated pyramid shape. In detail, the suture may be provided with the suture supporter having a truncated conical shape or a truncated pyramid shape and including a communication hole through which upper and lower end portions communicate with each other. The suture supporter may be coupled to the suture through the communication hole so that the upper end portion having a relatively smaller diameter from among the upper and lower end portions faces the first end of the suture. The suture supporter may include one or more cut portions that are cut in a longitudinal direction from a lower end portion face of the lower end portion having a relatively larger diameter from among the upper and lower end portions, wherein a part of the lower end portion may be removed so as to form one or more gaps formed from the lower end portion in a wall of the lower end portion. As such, if the suture supporter includes cut portions or gaps, an area contacting tissues is increased, and also fibrin or supporting tissues enter the gaps. Thus, when pulling the suture, a fixation ability may further be increased.

In addition, in the suture including the first and second ends, the suture supporter may be disposed at the first end of the suture. The suture supporter may have a truncated conical shape or a truncated pyramid shape and may include a communication hole through which upper and lower end portions communicate with each other. The suture supporter may have cut portions or gaps at a lower portion thereof. The suture supporter may be coupled to the suture through the communication hole so that the upper end portion having a relatively smaller diameter from among the upper and lower end portions faces the first end. Also, barbs may be formed on a surface of the suture.

There may be one or two or more suture supporters. The suture supporter may be disposed at the first end of the suture and may have a truncated conical shape or a truncated pyramid shape. The suture supporter may have cut portions or gaps at a lower end portion thereof.

In addition, there may be a single or two or more sutures. The suture may include the suture supporter that is disposed at the first end of the suture and has a truncated conical shape or a truncated pyramid shape. The suture supporter may have cut portions or gaps at a lower portion thereof. A needle may be disposed at the second end of the suture. The suture may include barbs and the barbs of the suture may be formed on a surface of the suture to be inclined toward the second end of the suture so that an angle ($\theta$) formed by a longitudinal axis of the suture and the barbs inclined toward the second end of the suture is an acute angle. According to another aspect of the present invention, there is provided a method of manufacturing a suture including a suture supporter. The suture supporter may have a truncated conical shape or a truncated pyramid shape and may include a communication hole through which upper and lower end portions communicate with each other. Furthermore, there is provided a method of manufacturing a suture including a suture supporter. The suture supporter may have a truncated conical shape or a truncated pyramid shape, may include a communication hole through which upper and lower end portions communicate with each other, and may include cut portions or gaps at a lower end portion thereof.

According to another aspect of the present invention, there are provided a method of using the suture provided in the present invention, a kit including the suture provided in the present invention, and an operation device including the suture provided in the present invention.

Advantageous Effects

The suture provided in the present invention may be used to safely perform an operation without making a knot when tightly adhering, supporting and fixing tissues to be sutured. The suture may be firmly maintained and fixed in a part to be sutured and may effectively holding tissues. In addition, when the kit provided in the present invention is used, an operation may be easily, simply, and effectively performed regardless of a skill of a doctor.

LIST OF MAJOR REFERENCE NUMERALS

10: suture
11: end connected with suture supporter (first end)
12: end not connected with suture supporter (second end)
20: suture supporter
21: upper end portion of suture supporter
22: lower end portion of suture supporter
23: cut portion formed at suture supporter
24: gap formed at suture supporter
25: communication hole of suture supporter
30: needle
40: barb
50: knot
70: long pipe of kit A
80: long pipe of kit B
90: rod of kit B
100: kit for surgical operation
101: tip (101a, 101b separable tip)
102: suture accommodation portion accommodating suture supporter
103: handle (103a, 103b: separable handle)
104: hollow pipe (104a, 104b: separable hollow pipe)
105: convex portion
106: concave portion

DETAILED DESCRIPTION OF THE INVENTION

The present invention will now be described more fully with reference to the accompanying drawings, in which exemplary embodiments of the invention are shown. The invention may, however, be embodied in many different forms, and should not be construed as being limited to the embodiments set forth herein; rather, these embodiments are provided so that this disclosure will be thorough and complete, and will fully convey the concept of the invention to one of ordinary skill in the art. In the drawings, the parts of the needle, suture supporter and barbs are exaggerated for clarity.

Figure 1:
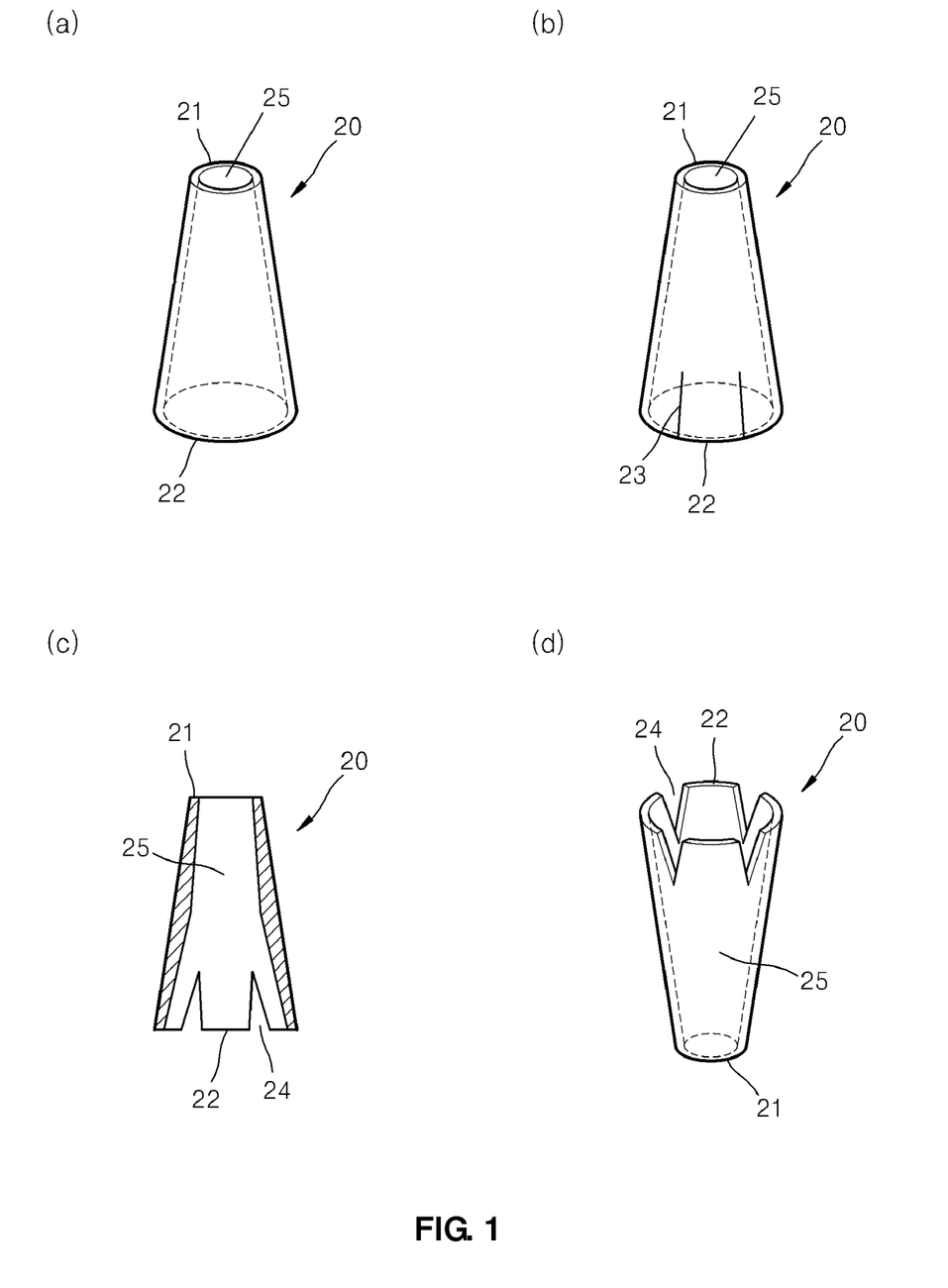
FIG. 1 is a view showing a suture supporter according to an embodiment of the present invention.

FIG. 1 is a view showing a suture supporter 20 according to an embodiment of the present invention. The suture supporter 20 has a truncated conical shape or a truncated pyramid shape. The suture supporter 20 includes a communication hole 25 through which upper and lower end portions communicate with each other, and a diameter of the communication hole 25 is larger than that of a suture (see FIG. 1(A)).

The suture supporter 20 according to an embodiment of the present invention may include one or more cut portions 23 that are cut in a longitudinal direction from a lower end portion 22 of the lower portion having a relatively larger diameter from among the upper and lower end portions (see FIG. 1(B)). Alternatively, a part of the lower portion is removed so as to form one or more gaps 24 formed from the lower end portion in a wall of the lower end portion (see FIGS. 1(C) and 1(D)). A length of the cut portion 23 and a size or shape of the gap 24 may be appropriately adjusted according to parts and purposes to use a suture.

The suture supporter 20 according to an embodiment of the present invention may be formed of a material not absorbed into a body or an absorbable material according to purposes. For example, the suture supporter 20 may be formed of nylon, polypropylene (for example, MESH), polyvinyliden fluoride, polyester, stainless steel, gold, titanium, silicon, medpore, gore-tex, mesh, polylactic acid, polydioxanone (PDO, PDS), or copolymer of lactic acid and glycolic acid, but the present invention is not limited thereto. If the suture supporter 20 is formed of an absorbable material, it is not necessary to remove the suture supporter 20 after performing a sutura of an inner part of the body.

The length of the suture supporter 20 according to an embodiment of the present invention may be, for example, about 1 to about 10 mm. However, the present invention is not limited thereto, and thus the length of the suture supporter 20 may be adjusted according to parts and purposes to use the suture supporter 20. From among holes of both ends portions of the suture supporter 20, a diameter of a relatively smaller hole is, for example, about 0.1 to about 2 mm, and a diameter of a relatively larger hole is, for example, about 0.5 to 5 mm. However, the present invention is not limited thereto, and the diameters of the holes may be adjusted according to thicknesses of a suture and purposes to use the suture.

As an embodiment of the present invention, when the suture supporter 20 has a truncated conical shape or a truncated pyramid shape and includes the communication hole 25 and when a suture has first and second ends, the suture supporter 20 is connected to the first end, and the suture may have barbs. The suture supporter 20 may include one or more cut portions 23 that are cut in a longitudinal direction from the lower end portion 22 of the lower portion having a relatively larger diameter from among the upper and lower end portions (see FIG. 1(B)), or a part of the lower portion is removed so as to form one or more gaps 24 formed from the lower end portion in a wall of the lower portion 22 (see FIGS. 1(C) and 1(D)).

The method includes a step of coupling the suture to the suture supporter 20 through the communication hole 25 so that an upper end portion 21 of the upper end having a relatively smaller diameter from among both the upper and lower ends of the suture supporter 20 faces the first end 11, and a step of forming a knot 50, which has a diameter larger than that of a hole of the upper end portion 21 of the suture supporter 20, between the first end 11 of the suture and the upper end portion 21 of the suture supporter 20 and forming an agglomerated portion of the suture by applying heat thereto, so that the suture supporter 20 is not separated from the suture. However, the present invention is not limited thereto.

According to an embodiment of the present invention, in the suture of the present invention, the other end portion not connected to the suture supporter 20, that is, the second end 12, may be used in a state coupled or uncoupled to a needle. Here, the needle used is manufactured of an non-absorbable material such as a metal material, or an absorbable material (for example, polylactic acid). The needle for a sutura may be formed in the shape of a straight line or a curve, and a point of the needle may have a shape that is widely used such as a rounded shape, a cut shape, or an extended shape.

Examples of a method of coupling a suture to a needle may include a method of inserting the suture into a hollow needle body and pressing the needle, a method of forming a hole (needle's eye) in the needle and inserting the suture into the hole, and the like. However, the present invention is not limited thereto, and various other methods may be used.

Figure 2:
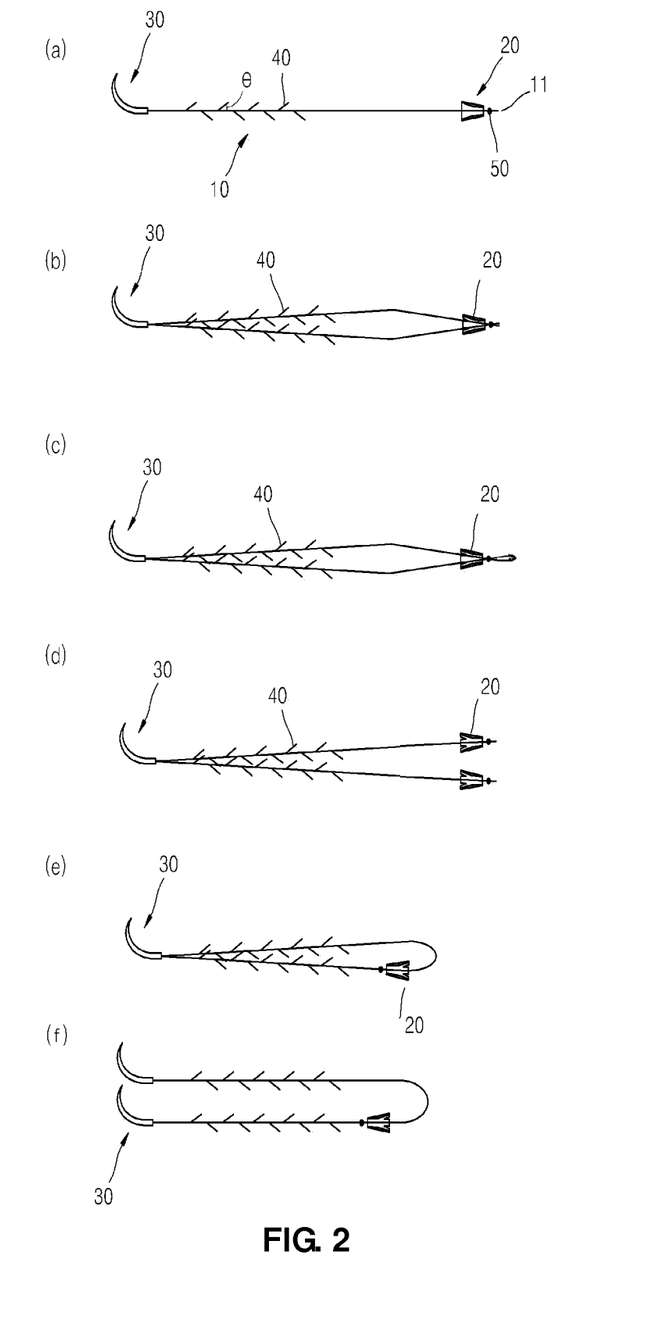
FIG. 2 is a view showing a suture including a suture supporter and a needle according to an embodiment of the present invention.

FIG. 2 is a view showing the suture including the first and second ends 11 and 12. In the suture, the suture supporter 20 has a truncated conical shape or a truncated pyramid shape and includes the communication hole 25 through which upper and lower end portions communicate with each other. The suture supporter 20 having cut portions or gaps at the lower end portion thereof is disposed at the first end 11 so that an upper end portion of the suture supporter 20 (the upper end portion 21 having a relatively smaller diameter from among the upper and lower end portions 21 and 22) faces the first end 11 of the suture connected to the suture supporter 20, and a needle 30 is disposed at the second end.

Barbs are formed on a surface of the suture so that angles between a longitudinal axis of the suture and the barbs are inclined in the same direction. The barbs are formed on the surface of the suture to be inclined so that an angle θ formed by the longitudinal axis of the suture and the barbs disposed at the second end of the suture is an acute angle. As such, if the barbs are formed so that the angle between the barbs and the suture has a pointed shape toward the second end of the suture not including the suture supporter 20, the suture may smoothly pass through a tissue when performing a sutura using the needle coupled to the second end of the suture. However, even if the needle is removed from the second end of the suture after the sutura, if the suture intends to move in a direction opposite to a direction of the sutura, the barbs may serve as a support to prevent the movement of the suture. Even though the needle is cut after the sutura, the suture is not pulled out, and thus it is not necessary to make a knot. In addition, the suture supporter 20 disposed at one end of the suture may serve as a knot that allows the suture not to be untied and may tightly fix the suture supporter 20 so that the suture supporter 20 does not move due to the cut portions or the gaps formed in the lower portion of the suture supporter 20 when pulling the suture while performing a sutura or lifting. Accordingly, the suture supporter 20 may stably maintain a lifting effect for a long time.

According to an embodiment of the present invention, one or more sutures including barbs may be used, and a number of sutures may be appropriately adjusted according to thicknesses of the sutures or purposes to use the sutures. Each suture may be a single suture or a multi suture that is twisted or woven. Here, the first end of each suture including barbs may be coupled to one suture supporter 20 (see FIGS. 2(B), 2(C), 2(E), and 2(F)), or alternatively, the first end of each suture may include a separate suture supporter (see FIG. 2(D)). In addition, second ends of two sutures may be coupled to one needle (see FIGS. 2(B), 2(C), 2(D), and 2(E)), or alternatively, different needles may be coupled to the seconds of two sutures, respectively (see FIG. 2(F)).

FIG. 2(B) shows two or more sutures in which front barbs and rear barbs are formed to be inclined in the same direction. In FIG. 2(B), one end parts of the suture are coupled to a needle and the other end parts thereof are coupled to the suture supporter 20. Here, the barbs are disposed to be inclined so that the angle θ formed by the longitudinal axis of the suture and the barbs disposed at the end part of the suture coupled to the needle is an acute angle. FIG. 2(C) shows another embodiment in which one or more sutures are folded in half and then both ends are coupled to the suture supporter 20 and the needle. In FIG. 2(C), the suture is formed so that front barbs and rear barbs formed in the suture are inclined in an opposite direction (for example, so that an angle between the front barbs and the longitudinal axis of the suture is less than 90° and the front barbs are inclined toward a front end of the suture and so that an angle between the rear barbs and the longitudinal axis of the suture is less than less than 90° and the rear barbs are inclined toward a rear end of the suture).

Figure 3:
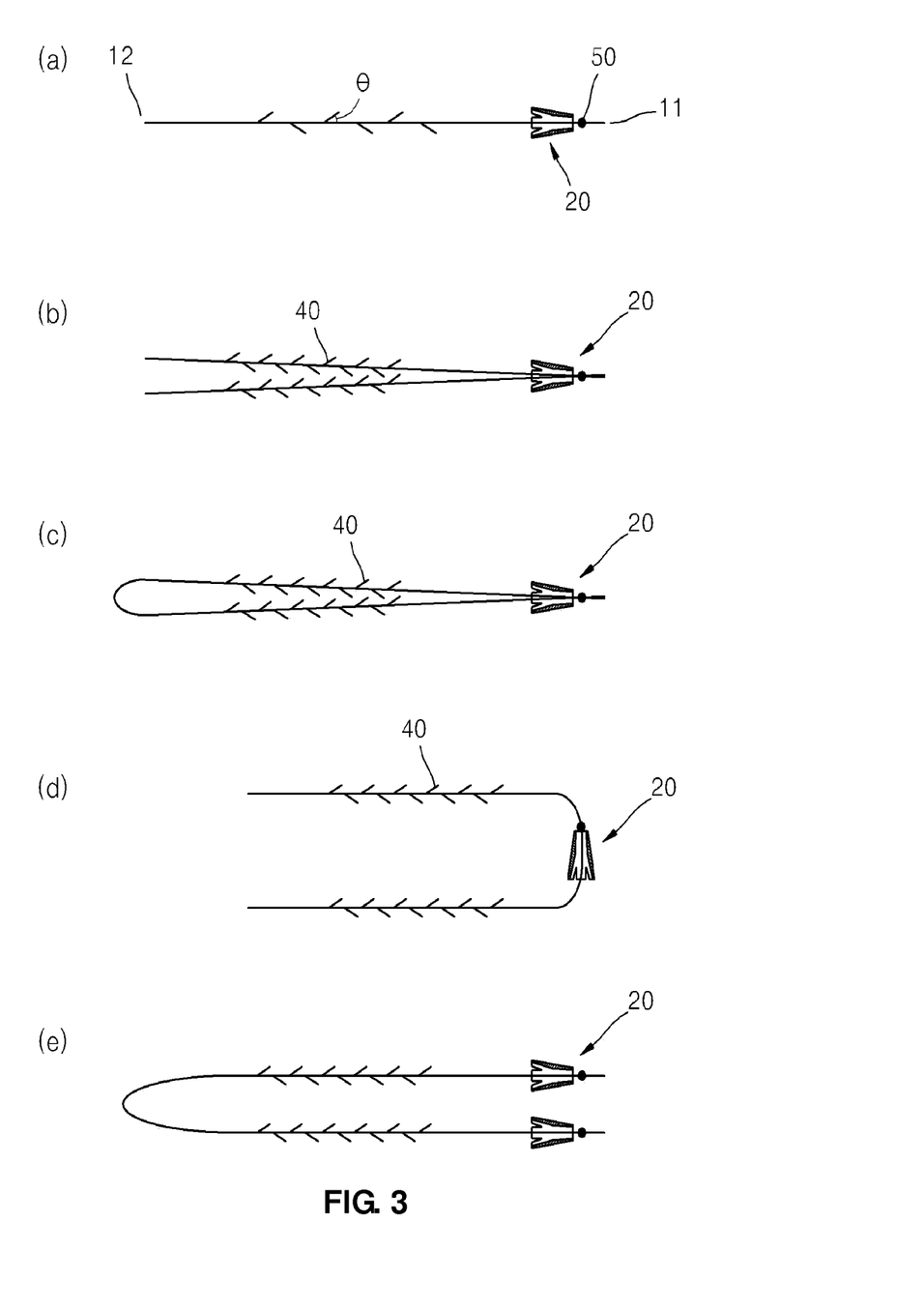
FIG. 3 is a view showing a suture including a suture supporter according to an embodiment of the present invention.

FIG. 3 shows a suture to which the suture supporter 20 is coupled which includes a communication hole through which upper and lower end portions communicate with each other and has a truncated conical shape or a truncated pyramid shape or the suture supporter 20 is coupled which includes a communication hole through which upper and lower end portions communicate with each other, has a truncated conical shape or a truncated pyramid shape, and has cut portions or gaps at a lower end portion of the suture supporter 20. The suture supporter 20 is coupled to the suture via the communication hole to be disposed at the first end 11 so that the upper end portion 21 (end portion having a relatively smaller diameter from upper and lower end portions) of the suture supporter 20 faces the first end 11 of the suture, and the needle is not disposed at the second end 12. The suture may include barbs on a surface thereof, and the barbs may be formed to be inclined toward the second end of the suture so that an angle θ formed by the longitudinal axis of the suture and the barbs is an acute angle.

According to an embodiment of the present invention, one or more sutures including barbs may be used, and a number of sutures may be appropriately adjusted according to thicknesses of the sutures or purposes to use the sutures. When two or more sutures are used, the sutures may pass through a communication hole of one suture supporter 20 to make a knot (see FIGS. 3(B) and 3(C)), or alternatively, one suture is coupled to the suture supporter 20 to pass through the communication hole of the suture supporter 20 (see FIG. 3(D)). FIGS. 3(C), 3(D), and 3(E) show an example in which one or more sutures, which are formed so that front barbs and rear barbs are inclined in an opposite direction, are folded in half and then one end of the suture is coupled to the suture supporter 20.

A suture including barbs is disclosed in Korean Patent Publication Nos. 10-2008-0039345 and 10-2005-0108494, Korean Utility Model No. 20-320005, U.S. Pat. No. 5,931, 855, and the like, and the contents are introduced in the present specification. Barbs may be arranged on a fiber according to any necessary configurations, and may be formed by using any appropriate methods including methods well-known in the art. Those methods may include injection molding using a knife, a laser, or press molding, stamping, and cutting. A necessary number of portions cut at an acute angle are formed in a suture. A size of barb may be appropriately adjusted according to purposes within the bounds of a common sense in the art. For example, a depth of the barb formed in the suture may be about 30 to 100 micron and may be adjusted according to a diameter of the suture. An interval between barbs formed on a surface of the suture may be about 100 micron to 1 mm or more.

The suture used in the present invention may be formed of, for example, a polymeric material, a metal material, a biological material, or the like. The suture may be formed of a non-absorbable material, for example, polypropylene, gold, stainless steel, titanium, nylon, polyvinyliden fluoride, polyester, or braided silk, or an absorbable material, for example, polydioxanone (PDO, PDS). However, the present invention is not limited thereto. In addition, the suture used in the present invention may be formed into a short fiber shape or a twisted shape.

Hereinafter, description will be given of a method of using a suture 10 including the suture supporter 20 at one end thereof, wherein the suture supporter 20 may include a communication hole through which upper and lower end portions communicate with each other and has a truncated conical shape or a truncated pyramid shape or may include cut portions or gaps at a lower end portion thereof and has a truncated conical shape or a truncated pyramid shape. The method may include the following processes.

1) a step of piercing a skin or a tissue using a needle so that a suture supporter is located in a predetermined position of the skin or the tissue and pushing a hollow pipe in the predetermined position of the skin or the tissue,
2) a step of inserting the suture 10 including the suture supporter 20 according to an embodiment of the present invention into the pipe so that the suture supporter 20 reaches the predetermined position,
3) a step pressing the suture supporter 20 having passed through the pipe inside the skin or the tissue from the outside, fixing the suture supporter 20 using a thin bar so as not to move, and removing only the pipe, and
4) a step of pushing the skin or the tissue while pressing the suture supporter 20 and pulling the suture.

Here, one or a plurality of sutures may be used in which a line of barbs are formed and includes the suture supporter 20 at one end thereof. Alternatively, the suture used here may be a suture in which two or more lines of barbs are formed may be coupled to one suture supporter 20. In the above-described method, the suture supporter 20 may serve as a knot that allows the suture not to be untied and may also allow the suture not to move and be fixed when puling the suture while performing a sutura or lifting. The suture supporter 20 having the cut portions or the gaps formed at the lower end portion thereof may further firmly fix the suture, and thus the suture supporter 20 may stably maintain a lifting effect for a long time.

When the barbs are formed to be inclined toward the second end so that the angle θ formed by the longitudinal axis of the suture and the barbs disposed at the second end of the suture is an acute angle, the formed barbs may prevent the suture from being pulled out in a direction opposite to the lifting by an angle between the barbs and a surface of the suture and may maintain a tissue in a pulled state. When inserting the suture into a long pipe, resistance against the tissue does not exist, and thus the suture may easily pass through the long pipe. In addition, even when removing the long pipe and pushing the tissue while pressing the suture supporter 20 and pulling the suture, the barbs formed such that an angle between the barbs and the suture is an acute angle do not greatly affect movement of the tissue, but if the tissue intends to return in an opposite direction, the barbs resist.

An embodiment of the present invention provides a device capable of easily performing an operation by using the suture provided in the present invention. The device provided in the present invention includes a kit (kit A) equipped with a suture and a suture positioning kit (kit B) for allowing a suture to be accurately positioned in a tissue.

Figure 4:
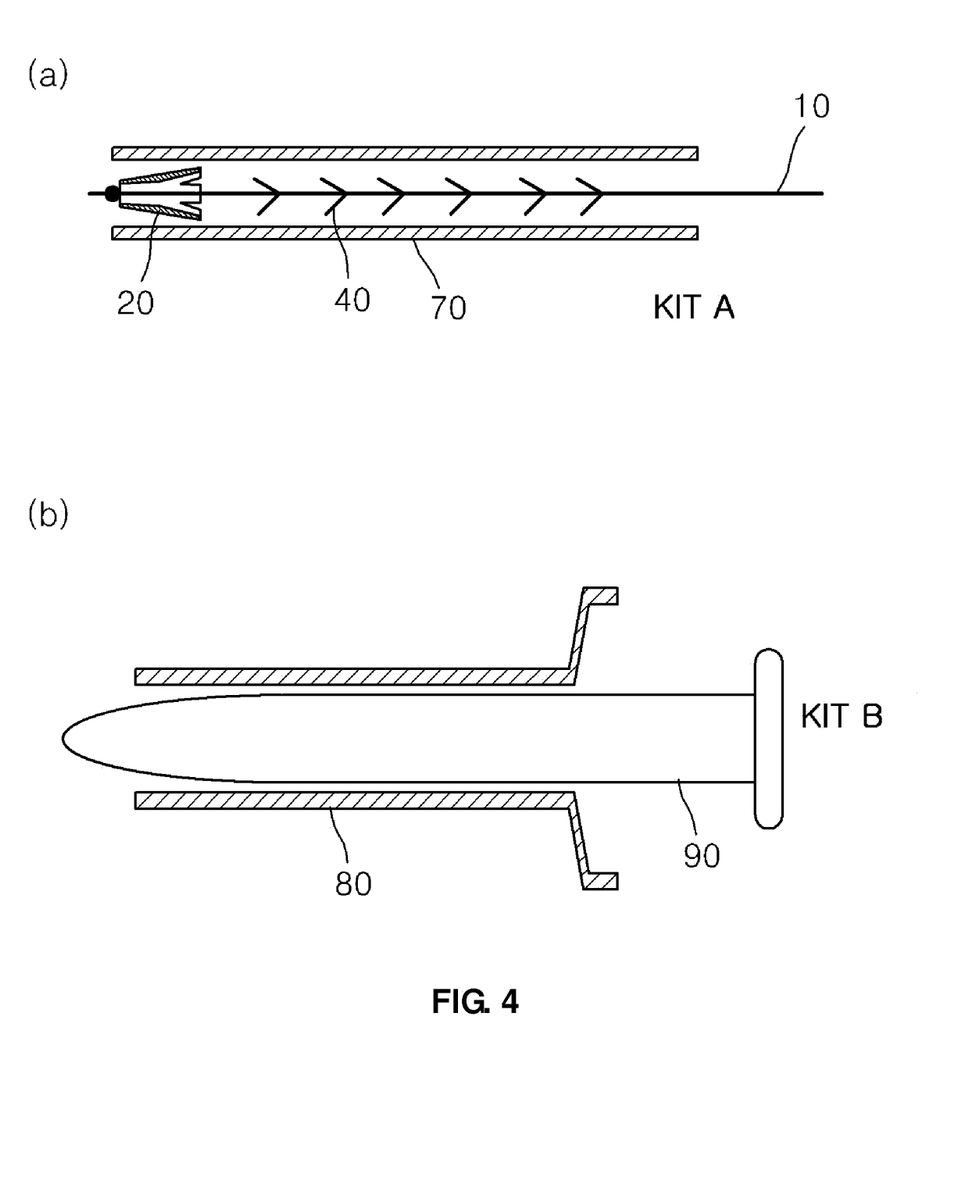
FIG. 4 is a view showing a kit including a suture according to an embodiment of the present invention.

The kit (kit A) equipped with a suture includes a hollow pipe 70 in which a hole through which both end portions communicate with each other is formed, and the suture installed in the hollow pipe 70. The suture has first and second ends, and the suture supporter 20 is disposed at the first end of the suture. The suture supporter 20 may have a truncated conical shape or a truncated pyramid shape and may have a communication hole through which upper and lower end portions communicate with each other. Alternatively, the suture supporter 20 may have a truncated conical shape or a truncated pyramid shape, may have a communication hole through which upper and lower end portions communicate with each other, and cut portions or gaps may be formed at the lower end portion thereof. The suture supporter 20 is coupled to the suture via the communication hole to be disposed at the first end of the suture so that the upper end portion of the suture supporter 20 faces the first end of the suture. The suture may include barbs on a surface thereof, and the barbs may be formed to be inclined toward the second end of the suture so that an angle θ formed by the longitudinal axis of the suture and the barbs disposed at the second end of the suture is an acute angle. In the kit A, the suture supporter 20 provided in the present invention is disposed in the hollow pipe 70 in which both end parts communicate with each other, and a suture including barbs on a surface thereof is inserted into the hollow pipe 70. Here, the suture supporter 20 is positioned at an end of the suture pierced into a tissue from among the both ends of the suture (see FIG. 4(A)). The suture supporter 20 may be positioned inside the hollow pipe 70 or outside of the end part of the hollow pipe 70, or may be positioned across the inside and the outside of the hollow pipe 70, when necessary. In the kit A, the communication hole of the hollow pipe 70 may have a diameter capable of accommodating the suture, and the diameter may be adjusted according to purposes.

The suture positioning kit (kit B) for allowing a suture to be accurately positioned in a tissue includes a hollow pipe 80 in which a communication hole through which both end portions communicate with each other is formed, and a rod 90 that is inserted into the communication hole of the hollow pipe 80, is formed to be longer than the hollow pipe 80, and has a pointed tip capable of being inserted into a body an one side thereof (see FIG. 4(B)). The rod 90 is formed of a material having strength to be pierced into a skin or a tissue, and if the pointed tip of the rod 90 has a blunt shape or a rounded shape, the damages of the tissue may be minimized.

The hollow pipe 80 of the kit B is shorter than the hollow pipe 70 of the kit A, and may have a diameter of the communication hole larger than that of the kit A so as to accommodate the kit A. The hollow pipe and the rod may be formed of any material that has a high hardness to be pierced into a metal or a tissue and is harmless to humans, for example, urethane or plastic. The hollow pipe 70 of the kit A and the hollow pipe 80 of the kit B may be provided with a handle at an end part thereof for convenience of an operation.

The device shown in FIG. 4 may be used by using a method including the following processes:

1) a step of pushing the kit B into a portion or a tissue to be sutured or lifted,
2) a step of removing only the rod 90 and leaving the hollow pipe 80,
3) a step of pushing the kit A into the hollow pipe 80 remaining in a tissue (here, a portion at which the suture supporter 20 is positioned is allowed to face the inside of the tissue),
4) a step of removing the hollow pipe 80 of the kit B and leaving the kit A in the tissue.
5) a step of pushing the suture supporter 20 using a thin bar into the tissue outside of the hollow pipe 70 of the kit A,
6) a step of removing the hollow pipe 70 of the kit A and the thin bar, and
7) a step pushing a skin (or outside of tissue) toward the suture supporter 20 while pulling a suture. If necessary, it is possible to allow the suture supporter 20 not to move by pushing the suture supporter 20 from the outside (for example, skin).

Figure 5:
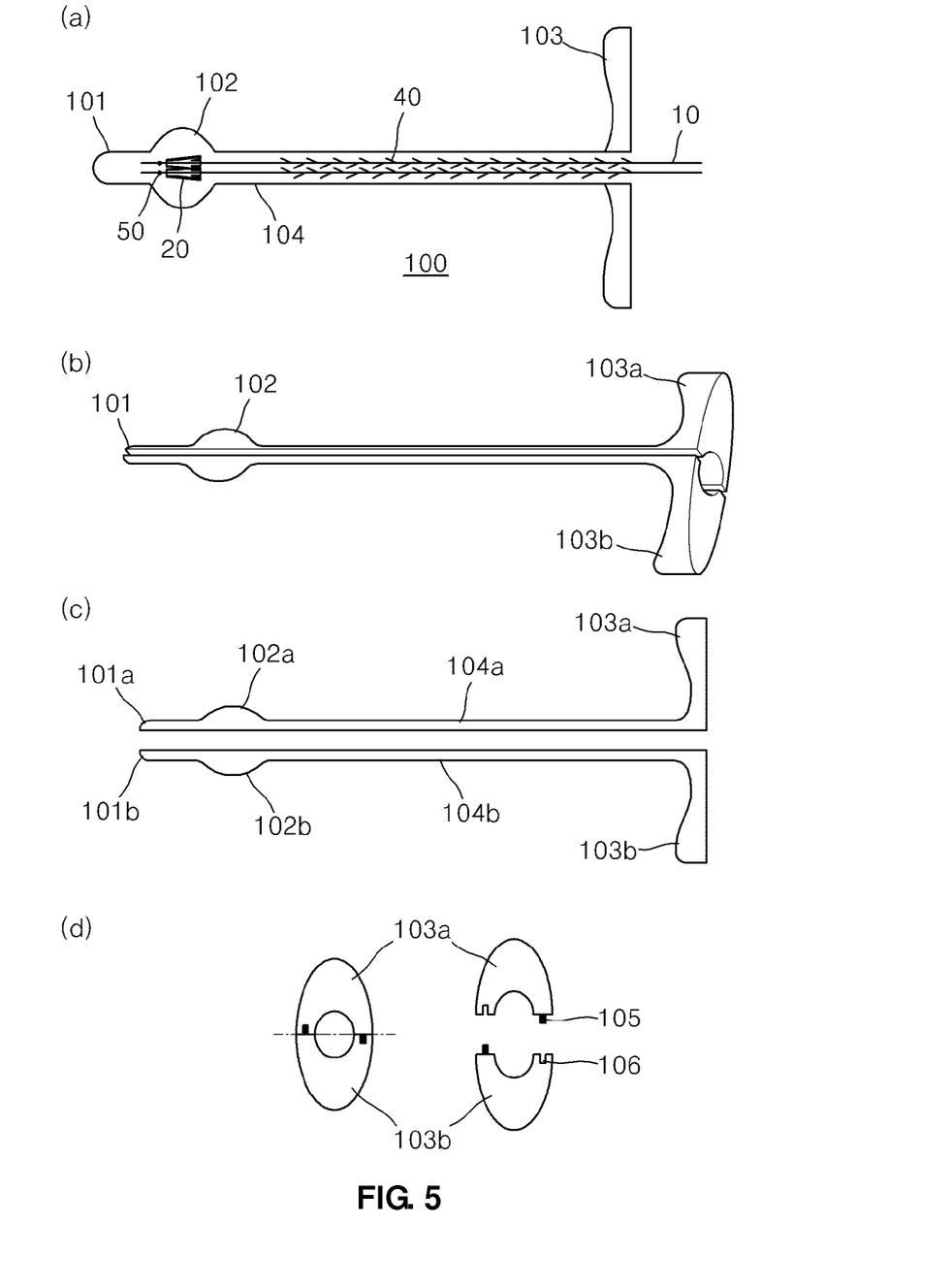
FIG. 5 is a view showing a kit including a suture according to an embodiment of the present invention.

The present invention also provides a kit that facilitates an operation using the suture provided in the present invention (see FIG. 5). The kit includes: i) a hollow pipe 104 including a front end provided with a tip that is formed to be tapered, a rear end provided with a handle 103, and an accommodation portion 102 accommodating the suture supporter 20 disposed in a suture around the front end and capable of being separated in a direction of a longitudinal axis connecting the front end and the rear end; and ii) the suture including the suture supporter 20 that is installed in the hollow pipe 104 and is provided in the present invention. FIG. 5(A) shows the hollow pipe 104 in which the suture including the suture supporter 20 is disposed.

Here, a tip of the front end of the hollow pipe 104 may be closed, or alternatively, a hole may be formed in the front end of the hollow pipe 104 to communicate with the rear end. The tip may be formed of a material having strength to pierce a tissue. If the tip is formed to be rounded, the damage of the tissue may be reduced. The accommodation portion 102 formed in the hollow pipe 104 is formed to extend from the front end portion and is a space capable of accommodating the suture supporter 20 disposed in the suture. A size and shape of the accommodation portion 102 may be appropriately adjusted according to a size and a number of the suture supporter 20 accommodated in the accommodation portion 102 (see FIG. 5(B)).

The hollow pipe 104 may be separated in a direction along a longitudinal axis connecting the front end and the rear end as shown in FIG. 5C. The hollow pipe 104 may be formed by placing the suture including the suture supporter 20 on one half portion 104*b* of the separated hollow pipe 104 and covering the other half portion 104*a* on the suture. Here, for example, a convex portion 105 may be formed in one of a half handle 103*a* and a half handle 103*b* at the junction of the half handle 103*a* and the half handle 103*b*, and a concave portion 106 may be formed in the other one of the half handle 103*a* and the half handle 103*b* at the junction of the half handle 103*a* and the half handle 103*b*, so that the half handle 103*a* and the half handle 103*b* may be stably fixed when coupling the half handle 103*a* and the half handle 103*b* to each other, thereby stably maintaining the hollow pipe 104 accommodating the suture (see FIG. 5(D) which is a top view of the handle 103). In addition, various methods may be performed of allowing the hollow pipe 104 formed by coupling separated two parts to each other to stably maintain its shape until a necessary time during an operation.

An operation may also be performed by using a method of pushing the hollow pipe 104 accommodating the suture into a part to be sutured or lifted from the tip 101, inserting a thin bar through a space of the hollow pipe 104 so as not to move the suture supporter 20, separating the hollow pipe 104 to sequentially remove the separated half portions 104*a* and 104*b*, and pushing a skin (or outside of tissue) toward the suture supporter 20 while pulling the suture.

The suture provided in the present invention may be used to safely perform an operation without making a knot when tightly adhering, supporting and fixing tissues to be sutured. The suture may be firmly maintained and fixed in a part to be sutured and may effectively holding tissues. In addition, when the kit provided in the present invention is used, an operation may be easily, simply, and effectively performed regardless of a skill of a doctor. While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

The present invention may be useful for the technical field related to the suture.

What is claimed is:

1. A suturing method comprising:
  providing a suture comprising
    a thread,
    a group of barbs projecting from the thread,
    a suture supporter connected to a first point of the thread, and
    a needle coupled to a second point of the thread,
    wherein each of the group of barbs projects from the thread such that an acute angle is formed between a projection of each of the group of barbs from the thread and an extension of the thread toward the suture supporter at the projection from the thread,
    wherein a through-hole is formed in the suture supporter, wherein the suture supporter is connected to the first point of the thread such that the thread passes through the through-hole of the suture supporter and forms a knot for preventing the suture supporter from being disconnected from the thread; and
  performing a suturing procedure using the suture, wherein performing the suturing procedure comprises:
    passing the needle through tissues in a forward direction, which causes the thread coupled to the needle to pass through the tissues in the forward direction that is generally from the second point to the first point of the thread when the thread extends straight, and
    subsequently removing the needle from the thread,
    wherein, upon performing the suturing procedure, the group of barbs is to inhibit the thread from moving the thread in a backward direction opposite the forward direction,
    wherein, upon performing the suturing procedure, the suture supporter is to inhibit the thread from moving the thread in the forward direction, wherein the suturing method does not comprise tying a knot subsequent to removing the needle from the thread.

2. The method of claim 1, wherein the suture supporter comprises a truncated conical shape or a truncated pyramid shape having the through-hole.

3. The method of claim 1, wherein the suture supporter comprises a tapered body extending between a first end and a second end of the suture supporter.

4. The method of claim 3, wherein the first end is smaller than the second end, wherein the suture supporter comprises at least one notch formed in the second end.

5. The method of claim 1, wherein the suture supporter comprises at least one notch formed therein.

6. The method of claim 1, wherein the barbs are generally regularly repeated along the thread.

7. The method of claim 1, wherein the thread is only one thread extending between the first point and the second point.

8. The method of claim 1, wherein the thread is referred to as a first thread, and the suture further comprises a second thread coupled to the needle and the suture supporter.

9. The method of claim 8, wherein the first and second threads are formed by folding a single extension of thread.

10. The method of claim 8, wherein the first and second threads are formed of two separate extensions of thread.

11. The method of claim 8, wherein the group of barbs projecting from the first thread is referred to as a first group of barbs, wherein the suture further comprises a second group of barbs projecting from the second thread such that an acute angle is formed between an extension of the second thread toward the suture supporter and a projection of each of the second group of barbs at a point of the projection.

12. The method of claim 1, wherein the thread is referred to as a first thread, wherein the suture supporter is referred to as a first suture supporter, wherein the first thread is coupled to the needle and the first suture supporter, wherein the suture further comprises a second thread and a second suture supporter, wherein the second thread is coupled to the needle and the second suture supporter.

13. The method of claim 12, wherein the group of barbs projecting from the first thread is referred to as a first group of barbs, wherein the suture further comprises a second group of barbs projecting from the second thread such that an acute angle is formed between an extension of the second thread toward the second suture supporter and a projection of each of the second group of barbs at a point of the projection.

* * * * *